(12) United States Patent
VanGompel et al.

(10) Patent No.: US 7,018,369 B2
(45) Date of Patent: Mar. 28, 2006

(54) DISPOSABLE PANT-LIKE UNDERGARMENT HAVING AN ELASTIC BAND ADJACENT THE WAIST OPENING

(75) Inventors: Paul VanGompel, Hortonville, WI (US); Russell Evan Thorson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 268 days.

(21) Appl. No.: 10/452,714

(22) Filed: May 30, 2003

(65) Prior Publication Data

US 2004/0243086 A1    Dec. 2, 2004

(51) Int. Cl.
*A61F 13/15*    (2006.01)

(52) U.S. Cl. .................. 604/396; 604/385.24
(58) Field of Classification Search .......... 604/385.01, 604/385.19, 385.22, 385.23, 385.24, 392–402, 604/385.27, 385.29
See application file for complete search history.

(56) References Cited

U.S. PATENT DOCUMENTS

| | | |
|---|---|---|
| 1,696,909 A | 1/1929 | Gillespie |
| 2,166,012 A | 7/1939 | La Maida |
| 2,544,620 A | 3/1951 | Steinert |
| 2,748,772 A | 6/1956 | Titone et al. |
| 2,749,912 A | 6/1956 | Teitler |
| 3,098,484 A | 7/1963 | Younger |
| 3,237,625 A | 3/1966 | Johnson |
| 3,368,563 A | 2/1968 | Scheier |
| 3,424,162 A | 1/1969 | Parravicini |
| 4,031,568 A | 6/1977 | Huff |
| 4,036,233 A | 7/1977 | Kozak |
| 4,059,973 A | 11/1977 | Gresillon |
| 4,227,531 A | 10/1980 | McLeod |
| 4,300,967 A | 11/1981 | Sigl |
| 4,319,572 A | 3/1982 | Widlund et al. |
| 4,327,448 A | 5/1982 | Lunt |
| 4,355,425 A | 10/1982 | Jones et al. |
| 4,437,860 A | 3/1984 | Sigl et al. |
| 4,450,026 A | 5/1984 | Pieniak et al. |

(Continued)

FOREIGN PATENT DOCUMENTS

EP    0 323 634 A2    7/1989

(Continued)

OTHER PUBLICATIONS

Van Gompel et al., WO 2004/108039 A1, WIPO International Search Report, Mar. 30, 2004.*

(Continued)

*Primary Examiner*—Tatyana Zalukaeva
*Assistant Examiner*—Michael G. Bogart
(74) *Attorney, Agent, or Firm*—Thomas J. Connelly (57) ABSTRACT

A disposable pant-like undergarment is disclosed having stretchable front and back panels. An elastic band is secured to at least one of the front and back panels. The elastic band has a retracted length less than the retracted length of the panel to which it is secured. An absorbent assembly including a liquid pervious bodyside liner, a liquid-impervious outer cover, and an absorbent positioned therebetween, is secured to the front and back panels. The absorbent assembly is capable of being folded to enable the front panel to overlap the back panel. A pair of seams joins the front panel, the back panel and the elastic band together at their side edges to form a pant-like undergarment having a waist opening and a pair of leg openings. The elastic band creates a snug fit at the waist opening.

26 Claims, 5 Drawing Sheets

U.S. PATENT DOCUMENTS

| | | |
|---|---|---|
| 4,486,192 A | 12/1984 | Sigl |
| 4,507,163 A | 3/1985 | Menard |
| 4,543,154 A | 9/1985 | Reiter |
| 4,563,185 A | 1/1986 | Reiter |
| 4,606,964 A | 8/1986 | Wideman |
| 4,610,685 A | 9/1986 | Raley |
| 4,615,695 A | 10/1986 | Cooper |
| 4,639,949 A | 2/1987 | Ales et al. |
| 4,663,220 A | 5/1987 | Wisneski et al. |
| 4,681,580 A | 7/1987 | Reising et al. |
| 4,707,398 A | 11/1987 | Boggs |
| 4,710,189 A | 12/1987 | Lash |
| 4,720,415 A | 1/1988 | Vander Wielen et al. |
| 4,724,184 A | 2/1988 | Killian et al. |
| 4,741,949 A | 5/1988 | Morman et al. |
| 4,743,241 A | 5/1988 | Igaue et al. |
| 4,747,846 A | 5/1988 | Boland et al. |
| 4,756,709 A | 7/1988 | Stevens |
| 4,762,521 A | 8/1988 | Roessler et al. |
| 4,770,656 A | 9/1988 | Proxmire et al. |
| 4,789,699 A | 12/1988 | Kieffer et al. |
| 4,808,176 A | 2/1989 | Kielpikowski |
| 4,816,026 A | 3/1989 | Richardson |
| 4,820,572 A | 4/1989 | Killian et al. |
| 4,850,989 A | 7/1989 | Villez |
| 4,863,779 A | 9/1989 | Daponte |
| 4,872,871 A | 10/1989 | Proxmire et al. |
| 4,895,568 A | 1/1990 | Enloe |
| 4,908,247 A | 3/1990 | Baird et al. |
| 4,909,804 A | 3/1990 | Douglas, Sr. |
| 4,923,742 A | 5/1990 | Killian et al. |
| 4,940,464 A | 7/1990 | Van Gompel et al. |
| 4,968,312 A | 11/1990 | Khan |
| 4,981,747 A | 1/1991 | Morman |
| 5,004,466 A | 4/1991 | Uda et al. |
| 5,019,066 A | 5/1991 | Freeland et al. |
| 5,163,932 A | 11/1992 | Nomura et al. |
| 5,169,706 A | 12/1992 | Collier et al. |
| 5,204,997 A | 4/1993 | Suzuki et al. |
| 5,226,992 A | 7/1993 | Morman |
| 5,260,126 A | 11/1993 | Collier et al. |
| 5,288,791 A | 2/1994 | Collier et al. |
| 5,336,545 A | 8/1994 | Morman |
| 5,366,793 A | 11/1994 | Fitts et al. |
| 5,385,775 A | 1/1995 | Wright |
| 5,486,273 A | 1/1996 | Widlund et al. |
| 5,500,063 A | 3/1996 | Jessup |
| 5,503,908 A | 4/1996 | Faass |
| 5,514,470 A | 5/1996 | Haffner et al. |
| 5,545,158 A | 8/1996 | Jessup |
| 5,554,145 A | 9/1996 | Roe et al. |
| 5,569,232 A | 10/1996 | Roe et al. |
| 5,575,783 A | 11/1996 | Clear et al. |
| 5,601,547 A | 2/1997 | Kato et al. |
| 5,607,416 A | 3/1997 | Yamamoto et al. |
| 5,622,581 A | 4/1997 | Ducker et al. |
| 5,624,424 A | 4/1997 | Saisaka et al. |
| 5,669,996 A | 9/1997 | Jessup |
| 5,683,376 A | 11/1997 | Kato et al. |
| 5,690,627 A | 11/1997 | Clear et al. |
| 5,711,832 A | 1/1998 | Glaug et al. |
| 5,735,839 A | 4/1998 | Kawaguchi et al. |
| 5,749,866 A | 5/1998 | Roe et al. |
| 5,772,649 A | 6/1998 | Siudzinski |
| 5,807,368 A | 9/1998 | Helmer |
| 5,827,259 A | 10/1998 | Laux et al. |
| 5,836,930 A | 11/1998 | Lantz et al. |
| 5,846,232 A | 12/1998 | Serbiak et al. |
| 5,855,574 A | 1/1999 | Kling et al. |
| 5,876,391 A | 3/1999 | Roe et al. |
| 5,904,673 A | 5/1999 | Roe et al. |
| 5,904,675 A | 5/1999 | Laux et al. |
| 5,906,604 A | 5/1999 | Ronnberg et al. |
| 5,916,206 A | 6/1999 | Otsubo et al. |
| 5,932,497 A | 8/1999 | Morman et al. |
| 5,947,948 A | 9/1999 | Roe et al. |
| 5,968,031 A | 10/1999 | Schmitz |
| 5,971,970 A | 10/1999 | Carlbark et al. |
| 6,129,720 A | 10/2000 | Blenke et al. |
| 6,132,409 A | 10/2000 | Vogt et al. |
| 6,135,975 A | 10/2000 | Johnstone |
| 6,187,425 B1 | 2/2001 | Bell et al. |
| 6,193,701 B1 | 2/2001 | Van Gompel et al. |
| 6,240,569 B1 | 6/2001 | Van Gompel et al. |
| 6,248,097 B1 | 6/2001 | Beitz et al. |
| 6,264,641 B1 | 7/2001 | Van Gompel et al. |
| 6,313,372 B1 | 11/2001 | Suzuki |
| 6,322,547 B1 | 11/2001 | Hansson |
| 6,322,552 B1 | 11/2001 | Blenke et al. |
| 6,323,389 B1 | 11/2001 | Thomas et al. |
| 6,325,787 B1 | 12/2001 | Roe et al. |
| 6,336,921 B1 | 1/2002 | Kato et al. |
| 6,336,922 B1 | 1/2002 | VanGompel et al. |
| 6,340,782 B1 | 1/2002 | Kling et al. |
| 6,358,350 B1 | 3/2002 | Glaug et al. |
| 6,361,527 B1 | 3/2002 | Van Gompel et al. |
| 6,364,863 B1 | 4/2002 | Yamamoto et al. |
| 6,375,646 B1 | 4/2002 | Widlund et al. |
| 6,387,471 B1 | 5/2002 | Taylor et al. |
| 6,454,750 B1 | 9/2002 | Vogt et al. |
| 6,464,677 B1 | 10/2002 | Noguchi et al. |
| 6,465,073 B1 | 10/2002 | Morman et al. |
| 6,478,785 B1 | 11/2002 | Ashton et al. |
| 6,482,278 B1 | 11/2002 | McCabe et al. |
| 6,541,679 B1 | 4/2003 | Betrabet et al. |
| 6,551,294 B1 | 4/2003 | Elsberg et al. |
| 6,551,430 B1 | 4/2003 | Glaug et al. |
| 6,570,056 B1 | 5/2003 | Tanzer et al. |
| 6,572,601 B1 | 6/2003 | Suprise et al. |
| 6,595,975 B1 | 7/2003 | Vogt et al. |
| 2002/0002021 A1 | 1/2002 | May et al. |
| 2002/0007148 A1 | 1/2002 | May et al. |
| 2002/0007164 A1 | 1/2002 | Boggs et al. |
| 2002/0009940 A1 | 1/2002 | May et al. |
| 2002/0019616 A1 | 2/2002 | Thomas |
| 2002/0104608 A1 | 8/2002 | Welch et al. |
| 2002/0119722 A1 | 8/2002 | Welch et al. |
| 2002/0128617 A1 | 9/2002 | Roe et al. |
| 2002/0152540 A1 | 10/2002 | Van Gompel et al. |
| 2002/0169432 A1 | 11/2002 | Fell et al. |
| 2003/0055389 A1 | 3/2003 | Sanders et al. |
| 2003/0088230 A1 | 5/2003 | Belogh et al. |
| 2003/0124303 A1 | 7/2003 | Price et al. |
| 2003/0125690 A1* | 7/2003 | Hermansson et al. .. 604/385.01 |
| 2003/0135191 A1 | 7/2003 | Price et al. |
| 2003/0135192 A1 | 7/2003 | Guralski et al. |
| 2004/0045924 A1 | 3/2004 | Naritomi et al. |
| 2004/0082933 A1* | 4/2004 | Karami ............... 604/393 |
| 2004/0122400 A1 | 6/2004 | Hancock-Cooke et al. |
| 2004/0122404 A1* | 6/2004 | Meyer et al. ......... 604/385.19 |
| 2004/0122405 A1 | 6/2004 | Van Gompel et al. |
| 2004/0122411 A1 | 6/2004 | Hancock-Cooke |
| 2004/0210205 A1 | 10/2004 | Vangompel et al. |
| 2004/0243085 A1 | 12/2004 | Veith et al. |
| 2004/0243089 A1 | 12/2004 | Veith et al. |
| 2005/0107763 A1* | 5/2005 | Matsuda et al. ............ 604/396 |
| 2005/0131365 A1* | 6/2005 | Sakaguchi .................. 604/367 |

FOREIGN PATENT DOCUMENTS

| | | |
|---|---|---|
| EP | 0 357 298 A2 | 3/1990 |
| EP | 0 404 648 A1 | 12/1990 |
| EP | 0 213 642 B1 | 4/1991 |
| EP | 0 456 885 A1 | 11/1991 |

| | | |
|---|---|---|
| EP | 0 460 467 A1 | 12/1991 |
| EP | 0 526 868 A2 | 2/1993 |
| EP | 0 528 282 A2 | 2/1993 |
| EP | 0 650 714 A1 | 5/1995 |
| EP | 0 597 331 B1 | 11/1997 |
| EP | 0 630 221 B2 | 11/2000 |
| EP | 1 072 243 A2 | 1/2001 |
| EP | 1 157 681 A2 | 11/2001 |
| EP | 1 184 017 A1 | 3/2002 |
| EP | 1 240 881 A2 | 9/2002 |
| EP | 1 247 505 A2 | 10/2002 |
| EP | 1 247 506 A2 | 10/2002 |
| EP | 1 249 214 A2 | 10/2002 |
| EP | 1 374 814 A1 | 1/2004 |
| EP | 1 393 702 A2 | 3/2004 |
| EP | 1 428 487 A1 | 6/2004 |
| GB | 2 253 131 A | 9/1992 |
| GB | 2 297 474 A | 8/1996 |
| JP | 03-176053 A | 7/1991 |
| JP | 03-195555 A | 8/1991 |
| JP | 03-205053 A | 9/1991 |
| JP | 04-089050 A | 3/1992 |
| JP | 04-354948 A | 12/1992 |
| JP | 11-318978 A | 11/1999 |
| JP | 2000-279447 A | 10/2000 |
| JP | 2003-339771 A | 12/2003 |
| JP | 2004-089403 A | 3/2004 |
| WO | WO 95/02382 A1 | 1/1995 |
| WO | WO 95/02383 A1 | 1/1995 |
| WO | WO 96/08224 A2 | 3/1996 |
| WO | WO 96/11236 A1 | 4/1996 |
| WO | WO 96/23466 A1 | 8/1996 |
| WO | WO 96/32083 A1 | 10/1996 |
| WO | WO 97/23180 A1 | 7/1997 |
| WO | WO 97/43994 A1 | 11/1997 |
| WO | WO 98/29251 A1 | 7/1998 |
| WO | WO 98/53785 A1 | 12/1998 |
| WO | WO 99/56688 A1 | 11/1999 |
| WO | WO 99/60967 A1 | 12/1999 |
| WO | WO 99/60968 A1 | 12/1999 |
| WO | WO 99/60971 A1 | 12/1999 |
| WO | WO 99/60972 A1 | 12/1999 |
| WO | WO 99/60974 A1 | 12/1999 |
| WO | WO 00/02511 A1 | 1/2000 |
| WO | WO 00/37005 A2 | 6/2000 |
| WO | WO 00/39201 A2 | 7/2000 |
| WO | WO 01/87212 A1 | 11/2001 |
| WO | WO 02/069871 A1 | 9/2002 |
| WO | WO 2003/002052 A1 | 1/2003 |
| WO | WO 03/017903 A1 | 3/2003 |
| WO | WO 03/28604 A1 | 4/2003 |
| WO | WO 2004/054490 A1 | 7/2004 |

OTHER PUBLICATIONS

American Society for Testing Materials (ASTM) Designation: D 2433-93 (Reapproved 2002), "Standard Test Methods for Rubber Thread," pp. 1-6, published Feb. 2003.

American Society for Testing Materials (ASTM) Designation: D 5459-95, (Reapproved 2001) "Standard Test Method for Machine Direction Elastic Recovery and Permanent Deformation and Stress Retention of Stretch Wrap Film," pp. 731-733, published Sep. 1995.

* cited by examiner

DISPOSABLE PANT-LIKE UNDERGARMENT HAVING AN ELASTIC BAND ADJACENT THE WAIST OPENING

BACKGROUND OF THE INVENTION

A disposable pant-like undergarment is designed for absorbing human exudate. The pant-like undergarment is similar in appearance, size and shape to a regular cloth underwear except that it is not designed to be laundered and reused two or more times. A disposable pant-like undergarment is intended to be worn by persons, including infants, toddlers, or adults, and is designed for single or temporary use. The disposable pant-like undergarment is meant to be disposed of after being used once instead of being laundered or dry cleaned for re-use. The disposable pant-like undergarment is designed to be pulled up around the user's torso without having to first open the undergarment in order to place it on a person's body. The stretchability of the material used to construct the disposable pant-like undergarment permits the undergarment to snugly conform to the anatomy of the user's torso. The disposable pant-like undergarment can be manufactured to be an infant diaper, a child training pant, an adult incontinence garment, a feminine menstrual pant, etc.

Some disposable pant-like undergarments manufactured today resemble regular cloth underwear in that they have a waist opening and a pair of leg openings. Such disposable pant-like undergarments can be pulled up around the torso of a user in a similar fashion as regular cloth underwear. It has been found that a disposable, absorbent pant-like undergarment is generally more discreet than a refastenable undergarment because it does not contain the extra material forming the hook or adhesive fasteners and loop or adhesive landing zone materials. A disposable pant-like undergarment tends to be sleeker, smoother and slimmer, especially around the waist opening. For this reason, many adults suffering from incontinence tend to prefer the pant-like design. Today, the absorbent crotch portion of some disposable pant-like undergarments tend to sag or droop once they fill up with a large quantity of body fluid, such as urine. As the crotch portion sags, an extra downward force is applied to the front and back panels that can cause the entire undergarment to slide downward on the user's torso. This creates an uneasy and uncomfortable feeling for the user. Therefore, there is a need for a disposable, pant-like undergarment that contains a structure that will resist downward sliding on the user's torso.

Now a disposable pant-like undergarment for absorbing human discharge has been invented that includes an elastic band that creates a snug fit at the waist opening. This snug fit prevents the undergarment from sliding downward on the user's torso as the absorbent crotch portion accumulates body fluid.

SUMMARY OF THE INVENTION

Briefly, this invention relates to a disposable pant-like undergarment for absorbing human body fluid and solid excrement. The pant-like undergarment includes a stretchable front panel and a stretchable back panel, each having a distal end, first and second side edges, and a retracted length measured between said first and second side edges. An elastic band is secured to at least one of the front and back panels and has first and second side edges. The elastic band is cantilevered outward from the distal end of the panel to which it is secured. The elastic band also has a retracted length less than the retracted length of the panel to which it is secured. The pant-like undergarment also includes an absorbent assembly that bridges across and is secured to the front and back panels. The absorbent assembly includes a liquid pervious bodyside liner, a liquid-impervious outer cover, and an absorbent positioned therebetween. The absorbent assembly is capable of being folded to enable the front panel to overlap the back panel. A pair of seams joins the front panel, back panel and elastic band together at the first and second side edges to form a pant-like undergarment having a waist opening and a pair of leg openings. The elastic band creates a snug fit at the waist opening and prevents the undergarment from sliding downward on the user's torso even after the absorbent assembly has taken in a large quantity of body fluid.

DETAILED DESCRIPTION

Figure 1:
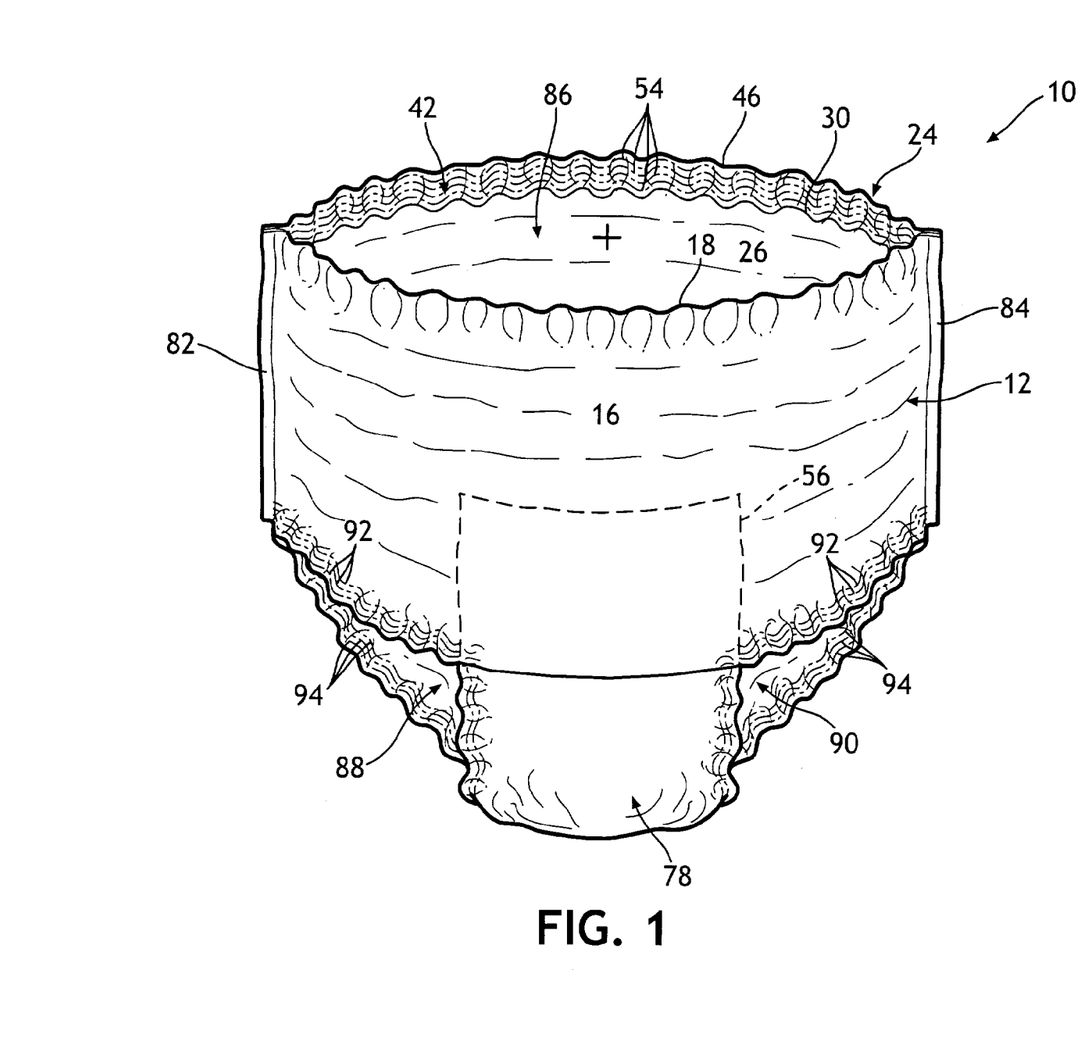
FIG. 1 is a perspective view of a disposable pant-like undergarment having an elastic band secured about at least a portion of said waist opening.

Referring to FIG. 1, a disposable pant-like absorbent undergarment 10 is depicted. The disposable pant-like undergarment 10 is intended to be worn by persons, including infants, toddlers, or adults, and is designed for a single or temporary use. The disposable pant-like undergarment 10 is meant to be disposed of after being used once instead of being laundered or dry cleaned for re-use. The disposable pant-like undergarment 10 is designed to be pulled up around the user's torso without having to first open the undergarment 10 in order to place it on a person's body. In FIG. 1, the disposable pant-like undergarment 10 is shown as it would appear just prior to being pulled up around a user's torso.

Figure 2:
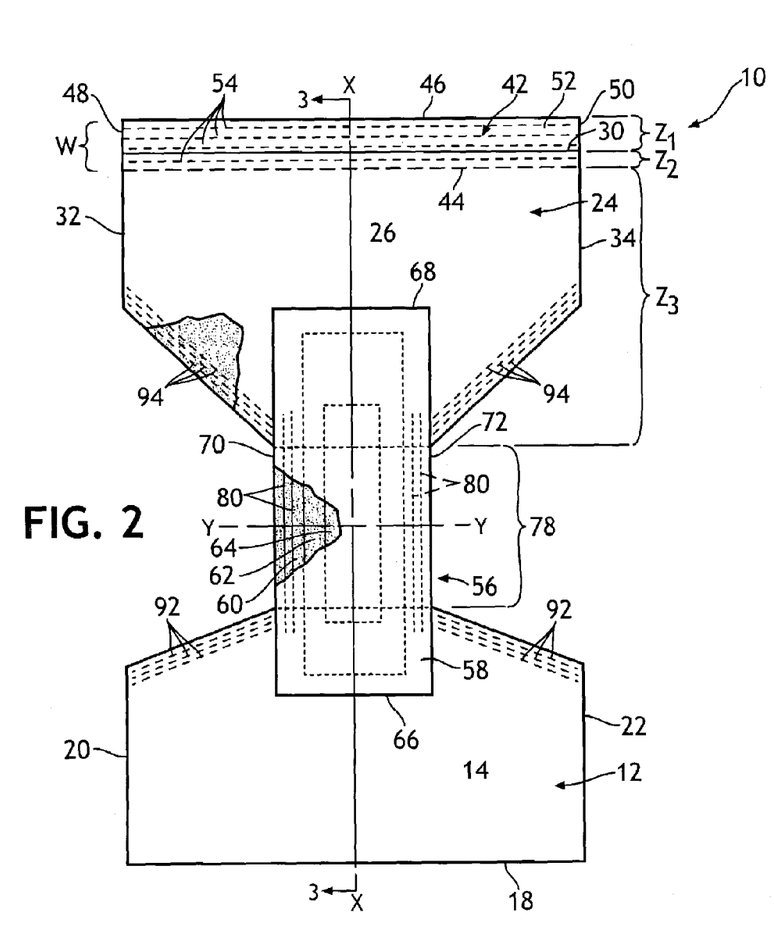
FIG. 2 is a plane view of the disposable pant-like undergarment shown in FIG. 1. depicting an absorbent assembly secured to the inner surface of the stretchable front and back panels and showing two partial cut away views of the construction of the absorbent assembly and the leg elastics.
Figure 3:
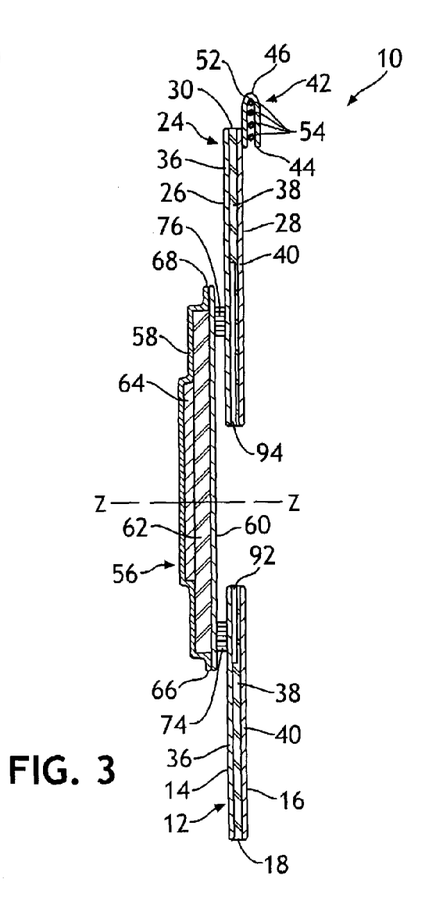
FIG. 3 is a side view of the disposable pant-like undergarment shown in FIG. 2 and taken along line 3—3.

Referring to FIGS. 2 and 3, the disposable pant-like undergarment 10 is depicted in an open position solely for the purpose of better showing the various components. The open undergarment 10 has a longitudinal central axis X-X, a transverse central axis Y-Y and a vertical central axis Z-Z. The pant-like undergarment 10 includes a stretchable front panel 12 having an inner surface 14, an outer surface 16, a distal end 18, a first side edge 20 and a second side edge 22.

By "stretchable" it is meant that the front panel 12 can be lengthened, widened, or extended by applying a force, such as by pulling. The stretchable front panel 12 is also capable of retracting to or towards its original pre-stretched length. By "retraction" it is meant that the front panel 12 can be shortened, or reduced in size or length. For example, a 1 inch (2.54 cm) strip of material can be stretched to about 2 inches (about 5 cm) and then when the stretching force is removed, the material will retract to or towards its original pre-stretched length of 1 inch (2.54 cm). The retracted length of the front panel 12 is measured as the distance between the first and second side edges, 20 and 22 respectively. The retracted length is measured after the force required to stretch the material has been removed. A common means of making the front panel 12 stretchable is to form it from an elastic component. By "elastic" is meant a material that is capable of quickly or immediately returning to an initial form or state after deformation, such as, for example, natural and synthetic rubbers and other materials known to those skilled in the art.

The disposable pant-like undergarment 10 also includes a stretchable back panel 24 having an inner surface 26, an outer surface 28, a distal end 30, a first side edge 32 and a second side edge 34. The same definitions recited above for the words "stretchable" and "retraction" apply to the back panel 24. The retracted length of the back panel 24 is measured as the distance between the first and second side edges, 32 and 34 respectively. The retracted length is measured after the force required to stretch the material has been removed.

The front and back panels, 12 and 24 respectively, are discontinuous from one another in the longitudinal direction. The inner surfaces 14 and 26 of the front and back panels, 12 and 24 respectively, are in direct contact with the user's skin and are also sometimes referred to as the bodyside surface. The outer surfaces 16 and 28 are situated opposite to the inner surfaces 14 and 26 and are spaced away from the user's skin. The outer surfaces 16 and 28 are also sometimes referred to as the garment facing surfaces since they can be in direct contact with the inner surfaces of the user's outer clothing.

The front and back panels, 12 and 24 respectively, are formed from a stretchable material. Desirably, the stretchable material is an elastic material or an elastic laminate that contains two or more layers wherein at least one of the layers is elastic. By "layer" it is meant a single elastic sheet, an elastic film, an elastic net like material or a plurality of elastic strands. When a plurality of elastic strands is utilized, they can be positioned between two or more outer layers. Each of the front and back panels, 12 and 24 respectively, is formed such that essentially the entire panel 12 and 24 is capable of being stretched and is also capable of being retracted. By "essentially the entire" is meant that approximately about 90% to 100% of the front panel 12 is stretchable and retractable and approximately about 90% to 100% of the back panel 22 is stretchable and retractable.

Referring to FIG. 3, each of the front and back panels, 12 and 24 respectively, are shown being formed as a three-layer laminate. Each of the front and back panels, 12 and 24 respectively, includes a first layer 36, a second or middle layer 38, and a third layer 40. The first and third layers, 36 and 40 respectively, are the outer layers and can be formed from the same material or from different materials. The first and third layers, 36 and 40 respectively, can be constructed from natural or synthetic fibers and can be a woven or non-woven material. The second or middle layer 38 has the elastic properties and is sandwiched between the first and third layers, 36 and 40 respectively. It should be noted that one or both of the outer layers 36 or 40 can be made from an elastic material, if desired. The front and back panels, 12 and 24 respectively, can also be formed as a two layer laminate with at least one of the layers being elastic, if desired.

The elastic laminate provides stretch and retraction in at least one direction. The stretch and retraction can be in one direction or in two or more directions. Desirably, the stretch and retraction of the front and back panels, 12 and 24 respectively, are in a direction approximately parallel to the transverse axis Y-Y. The transverse direction extends laterally across the torso from the left hip to the right hip. More desirably, the stretch and retraction of the front and back panels, 12 and 24 respectively, are in at least two directions, one direction being approximately parallel to the longitudinal axis X-X and the other direction being angled thereto. Most desirably, the stretch and retraction of the front and back panels, 12 and 24 respectively, are in multiple directions, or stated another way, in three or more directions extending over an arc of 360 degrees. The ability of the front and back panels, 12 and 24 respectively, to retract will provide a restrictive force during use of the disposable pant-like undergarment 10 to ensure that it snugly conforms to the anatomy of the wearer's torso.

Desirably, the front and back panels, 12 and 24 respectively, are constructed from a stretch bonded laminate (SBL). Exemplary SBL materials are described in U.S. Pat. No. 4,720,415 which is hereby incorporated by reference and made a part hereof. In the stretch bonded laminate, the elastic core or middle layer 38 is elongated before the two outer nonwoven layers 36 and 40 are attached. The attachment can be by an adhesive, by heat, by pressure, by a combination of heat and pressure, etc. Another material option for the front and back panels, 12 and 24 respectively, is a necked bonded laminate (NBL). The NBL material is also a three layer laminate but the elastic core or middle layer 38 is not pre-stretched prior to being attached to the two outer nonwoven layers 36 and 40. The outer layers 36 and 40 are necked stretched before the elastic core or middle layer 38 is attached to them. Exemplary NBL materials are described in U.S. Pat. No. 5,336,545 which is hereby incorporated by reference and made a part hereof. Other examples of elastomeric materials that can be used for the front and back panels, 12 and 24 respectively, include a continuous filament stretch bonded laminate (CFSBL), a vertical filament laminate (VFL), a necked stretch bonded laminate (NSBL) and a necked thermal laminate (NTL). Combinations of the above materials can also be used. Exemplary CFSBL materials are described in U.S. Pat. No. 5,385,775 which is hereby incorporated by reference and made a part hereof.

It should also be noted that the front and back panels, 12 and 24 respectively, can be constructed from an elastic film that is capable of being stretched in at least one direction and desirably in both the machine direction and the cross-direction. Alternatively, the front and back panels, 12 and 24 respectively, can be an elastic nonwoven that has a machine direction stretch or a cross-direction stretch. Extensible materials can also be used to form the front and back panels, 12 and 24 respectively, of the pant-like undergarment 10. Various other stretchable and elastic materials can be used which are known to those skilled in the art.

Alternatively, the front and back panels, 12 and 24 respectively, can be formed from two outer layers 36 and 40 with a plurality of elastic strands sandwiched therebetween. The elastic strands can be formed from LYCRA®. LYCRA® is a registered trademark of E. I. Du Pont De Nemours & Co., having an office at 1007 Market Street, Wilmington, Del. 19898. The elastic strands can be aligned approximately parallel to one another or be angled or skewed relative to one another. The elastic strands can also be uniformly or randomly spaced apart from one another. The elastic strands can vary in shape, size, configuration, and/or length. The diameter and/or cross-sectional configuration of the elastic strands, the decitex (weight in grams per 10,000 meters of a strand) of the elastic strands, and the tension imparted into the elastic strands can all be varied to suit one's particular product needs. The elastic strands can have a round, semicircular, square, rectangular, oval or some other geometrical configuration. The elastic strands can overlap, intersect or crisscross at least one other elastic strand. The various ways of positioning, orienting, and adhering the elastic strands to the two outer layers 36 and 40 are well known to those skilled in the art.

Referring again to FIGS. 1–3, the disposable pant-like undergarment 10 also includes an elastic band 42. The elastic band 42 can be secured to only the front panel 12 or to only the back panel 24. Desirably, the elastic band 42 is secured to at least one of the front and back panels, 12 and 24 respectively. In FIGS. 1–3, the elastic band 42 is shown being secured to the outer surface 28 of the back panel 24 in a semi-stretched condition. By "semi-stretched" is meant that the elastic band 42 has not fully retracted to its original length. It should be noted that the elastic band 42 can be secured to the inner surface 26 if desired. Also, the elastic band 42 can be secured to both of the front and back panels, 12 and 24 respectively, as is depicted in the alternative embodiment, see FIGS. 4–6. The elastic band 42 can be secured to the back panel 24 by using ultrasonics, by a thermal bond, by adhesive, by heat, by pressure, by a combination of heat and pressure, or a combination of any of the above. The elastic band 42 can also be secured to the back panel 24 by a mechanical attachment, such as by sewing with thread. Other means known to those skilled in the art can also be used to secure the elastic band 42 to the back panel 24.

It should also be noted that the elastic band 42 can be integrally formed with the front and/or back panels 12 and 24, if desired. Furthermore, the elastic band 42 could be sandwiched between the first and third layers, 36 and 40 respectively, of the front and back panels, 12 and 24 respectively. Alternatively, the elastic band 42 could be sandwiched between the first and second layers, 36 and 38 respectively, or the second and third layers, 38 and 40 respectively, of the front and back panels, 12 and 24 respectively.

The elastic band 42 has a first end 44, a second end 46, a first side edge 48 and a second side edge 50. The first end 44 overlaps a portion of the outer surface 28 of the back panel 24 while the second end 46 is spaced away from the distal end 30 of the back panel 24. The elastic band 42 is cantilevered outward from the distal end 30. By "cantilevered" it is meant that the elastic band 42 projects outward beyond the distal end 30 and is supported only at a location approximate the first end 44. The elastic band 42 has a width (w) that can range from between about 3 millimeters (mm) to about 150 mm. Desirably, the width (w) of the elastic band 42 ranges from between about 5 mm to about 100 mm. More desirably, the width (w) of the elastic band 42 ranges from between about 10 mm to about 50 mm. Most desirably, the width (w) of the elastic band 42 ranges from between about 12 mm to about 25 mm. The amount the elastic band 42 overlaps the back panel 24 can vary from between about 1 millimeter to a distance equal to about 75% of the width (w) of the elastic band 42. Desirably, the amount the elastic band 42 overlaps the back panel 24 ranges from between about 2 mm to about 25 mm. More desirably, the amount the elastic band 42 overlaps the back panel 24 ranges from between about 3 mm to about 15 mm. Most desirably, the amount the elastic band 42 overlaps the back panel 24 ranges from between about 4 mm to about 10 mm.

The elastic band 42 also has a retracted length measured as the distance between the first and second side edges, 48 and 50 respectively. The retracted length is measured after the force required to stretch the elastic band 42 has been removed. The retracted length of the elastic band 42 is less than the retracted length of the front or back panels, 12 or 24 respectively, to which it is secured. This means that the elastic band 42 will retract to a shorter length than the panel to which it is secured once the force needed to stretch the elastic band 42 has been removed. For example, in a small size, adult care incontinence undergarment, if the back panel 24 has a retracted length of about 13 inches (about 330 mm), the elastic band 42 can have a retracted length of about 12.5 inches (about 318 mm). This difference of about 0.5 inches (about 12 mm) means that the elastic band 42 will provide a snugger or tighter fit around the wearer's torso than the fit provided by the back panel 24. Desirably, the elastic band 42 has a retracted length that is at least 2% less than the retracted length of the panel to which it is secured. More desirably, the elastic band 42 has a retracted length that is at least 5% less than the retracted length of the panel to which it is secured. Still more desirably, the elastic band 42 has a retracted length that is at least 10% less than the retracted length of the panel to which it is secured. Most desirably, the elastic band 42 has a retracted length that is at least 15% less than the retracted length of the panel to which it is secured.

Another way of describing the retracted length of the elastic band 42 is to mention specific distances. The elastic band 42 should have a retracted length that is at least about 0.25 inches (about 6 mm) shorter than the retracted length of the panel to which it is secured. More desirably, the elastic band 42 should have a retracted length that is at least about 0.5 inches (about 12 mm) shorter than the retracted length of the panel to which it is secured. Still more desirably, the elastic band 42 should have a retracted length that is at least about 0.75 inches (about 19 mm) shorter than the retracted length of the panel to which it is secured. Most desirably, the elastic band 42 should have a retracted length that is at least about 1 inch (about 25 mm) shorter than the retracted length of the panel to which it is secured. The exact amount by which the retracted length of the elastic band 42 is shorter than the retracted length of the panel to which it is secured will depend upon various factors including: the distance between the first and second side edges, 32 and 34 respectively, of the two materials, the type of material from which the elastic band 42 and the panel is formed, the elastic tension in each material, the thickness of each material, the overall surface area of each material, etc.

Referring again to FIGS. 2 and 3, the elastic band 42 is shown constructed from a non-elastic member 52 having one or more elastic strands 54 secured thereto. The non-elastic member 52 can be formed from various woven or non-woven materials. An example of a non-woven material that can be used is polypropylene spunbond. The non-elastic member 52 can also be a laminate of two or more layers, if desired. The elastic strands 54 can be formed from LYCRA®. LYCRA® is a registered trademark of E. I. Du Pont De Nemours & Co., having an office at 1007 Market Street, Wilmington, Del. 19898. At least one of the elastic strands 54 in the elastic band 42 can extend from the first side edge 48 to the second side edge 50. Desirably, all of the elastic strands 54 in the elastic band 42 will extend from the first side edge 48 to the second side edge 50, as is depicted in FIG. 2. Alternatively, at least one of the elastic strands 54 in the elastic band 42 does not extend from the first side edge 48 to the second side edge 50. For example, one or more of the elastic strands 54 in the elastic band 42 can extend over only a portion of the distance located between the first and second side edges 48 and 50, see FIG. 5.

The elastic strands 54 can be aligned approximately parallel to one another or be angled or skewed relative to one another. The elastic strands 54 can also be uniformly or randomly spaced apart from one another. The elastic strands 54 can vary in shape, size, configuration, and/or length. The diameter and/or cross-sectional configuration of the elastic strands 54, the decitex (weight in grams per 10,000 meters of a strand) of the elastic strands 54, and the tension imparted into the elastic strands 54 can all be varied to suit one's particular product needs. The elastic strands 54 can have a round, semi-circular, square, rectangular, oval or some other geometrical configuration. The elastic strands 54 can overlap, intersect or crisscross at least one other elastic strand 54. The various ways of positioning, orienting, and adhering the elastic strands 54 to the non-elastic member 52 are well known to those skilled in the art.

The number of elastic strands 54 can range from 1 to well over 100. The exact number of elastic strands 54 that are present will depend on the width (w) of the elastic band 42, the diameter of each elastic strand 54, the arrangement of the elastic strands 54 on the non-elastic member 52, etc. Desirably, from about 2 to about 50 elastic strands 54 are present in the elastic band 42. More desirably, from about 3 to about 25 elastic strands 54 are present in the elastic band 42. Most desirably, from about 4 to about 10 elastic strands 54 are present in the elastic band 42. In FIGS. 2 and 3, four elastic strands 54 are depicted on the elastic band 42.

Figure 4:
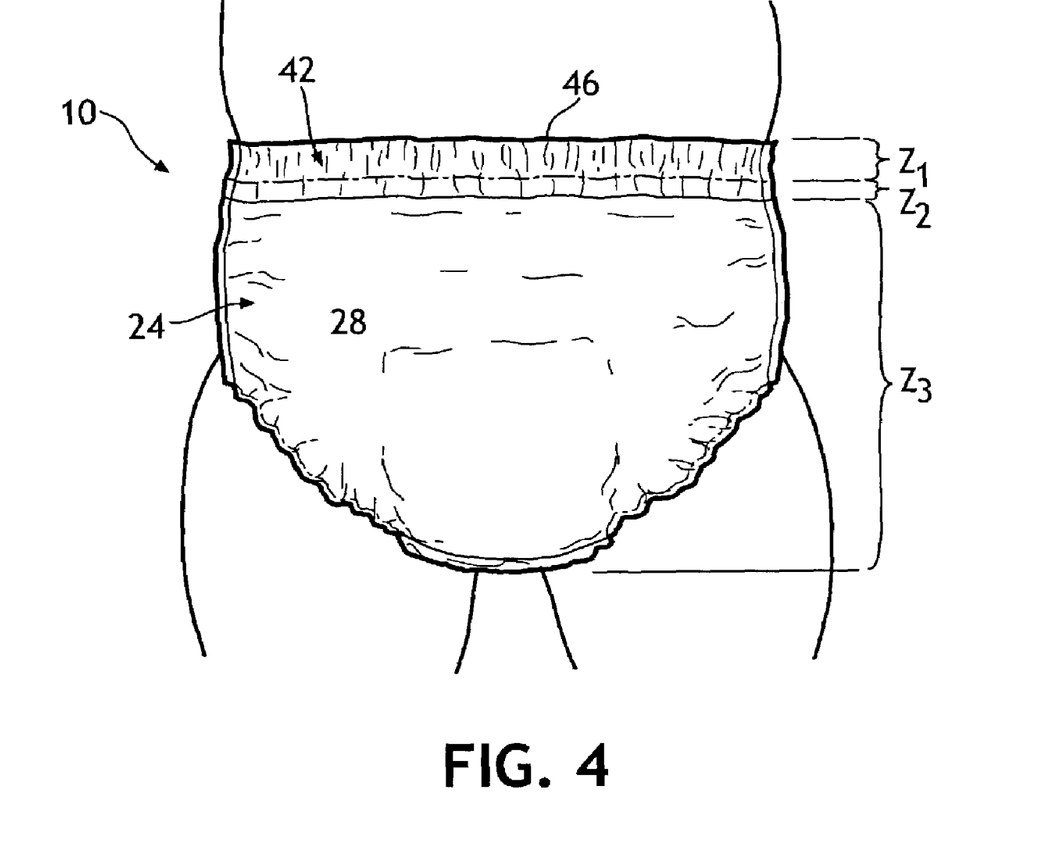
FIG. 4 is a view of a person's buttock and rear torso when wearing the disposable pant-like undergarment shown in FIG. 1 depicting three different stretchable zones.

Referring now to FIGS. 2–4, one can see that the non-elastic member 52 is depicted as being folded in half such that the four elastic strands 54 are located inside the fold. One will notice that three of the elastic strands 54 are located in a first zone ($z_1$) while one of the elastic strands 54 is located in a second zone ($z_2$) where the elastic band 42 overlaps the back panel 12. The remaining area of the back panel 12 forms a third zone ($z_3$). The force needed to stretch the material in the second zone ($z_2$) from its retracted length is greater than the force needed to stretch the material in the first zone ($z_1$) from its retracted length. In turn, the force needed to stretch the material in the first zone ($z_1$) from its retracted length is greater than the force needed to stretch the material in the third zone ($z_3$) from its retracted length. This zone differentiation of ($z_2 > z_1 > z_3$) is shown in FIG. 4. This zone differentiation is advantageous for it means that the material in the second zone ($z_2$) requires the greatest amount of force to stretch the material to a more open configuration from its retracted length. The importance of this is that the anatomy of most wearer's of the undergarment 10 dictates an increase in circumference as one moves downward from the area approximate the belly button to the hip area. The circumference of the torso gets larger as one moves downward away from the user's waist, which is located approximate the belly button, to a maximum hip circumference before tapering off again as one approaches the thigh area.

The second zone ($z_2$) is spaced away from the waist opening of the disposable undergarment 10. The distance that the second zone ($z_2$) is spaced away from the waist opening can range from between about 5 mm to about 100 mm. Desirably, the distance that the second zone ($z_2$) is spaced away from the waist opening can range from between about 8 mm to about 50 mm. More desirably, the distance that the second zone ($z_2$) is spaced away from the waist opening can range from between about 12 mm to about 30 mm. Most desirably, the distance that the second zone ($z_2$) is spaced away from the waist opening can range from between about 18 mm to about 25 mm. This means that the second zone ($z_2$) is distal the waist opening and adjacent to the maximum circumference of the wearer's torso. Since the force needed to enlarge the size of the second zone ($z_2$) is the greatest and the amount the second zone ($z_2$) would have to expand in order to slide downward over the hips is also large, the likelihood of the undergarment being able to slide downward towards the wearer's thighs is reduced. In other words, the second zone ($z_2$) is the most effective in holding the disposable undergarment 10 in proper position around the wearer's torso even when additional body fluid is released into the undergarment 10.

Returning now to FIG. 3, the non-elastic member 52 of the elastic band 42 is shown being folded over upon itself and having the fold be aligned adjacent to the second end 46. This configuration provides for a smooth, upper edge. The folded non-elastic member 52 will assure that no sharp or abrasive material edge is present against the wearer's skin. It should be noted that the non-elastic member 52 does not have to be folded if one wishes to use a different structure. For example, the non-elastic member 52 can consist of a single layer to which the elastic strands 54 are secured or it can be constructed from two or more layers, with the elastic strands 54 sandwiched therebetween.

It should be noted that even though the elastic band 42 has been described as containing one or more elastic strands 54, it is also possible to form the elastic band 42 from a stretchable, elastic material or from a stretchable laminate that contains two or more layers wherein at least one of the layers is elastic. By "layer" it is meant a single elastic sheet, an elastic film, an elastic net-like material, etc. The laminate could be constructed of the same or similar materials as was described above with reference to the front and back panels, 12 and 24 respectively.

Referring again to FIGS. 1–3, the disposable pant-like undergarment 10 also includes an absorbent assembly 56. The absorbent assembly 56 includes a liquid pervious bodyside liner 58, a liquid-impervious outer cover 60, and an absorbent 62 positioned therebetween. A surge layer 64 can be optionally used, which is located between the bodyside liner 58 and the absorbent 62. The surge layer 64 can function to rapidly acquire and temporarily retain body fluid, such as urine, before it can be absorbed into the absorbent 62. Desirably, the surge layer 64 is also capable of wicking body fluid lengthwise and/or widthwise across its surface as well as directing the body fluid downward in a z-direction, toward the absorbent 62.

Referring again to FIGS. 2 and 3, the absorbent assembly 56 has a first end 66, a second end 68, a first side edge 70 and a second side edge 72. The absorbent assembly 56 is shown secured to the inner surface 14 of the front panel 12 approximate the first end 66 by an attachment 74. The absorbent assembly 56 is also secured to the inner surface 26 of the back panel 24 approximate the second end 68 by an attachment 76. Alternatively, the absorbent assembly 56 can be secured to the outer surfaces 16 and 28 of the front and back panels, 12 and 24 respectively, if desired. The absorbent assembly 56 can be secured to the front and back panels, 12 and 24 respectively, after each panel has been stretched a predetermined amount. By attaching the absorbent assembly 56 to the inner surfaces 14 and 26 of the front and back panels, 12 and 24 respectively, the absorbent assembly 56 is capable of being in direct contact with the wearer's body.

The attachments 74 and 76 can be by various means and can include permanent attachments as well as removable or releasable attachments. Desirably, the attachments 74 and 76 are permanent attachments where they are not designed to be removed without destroying the bond. The attachments 74 and 76 can be formed by using glue, adhesive, ultrasonic bonds, thermal bonds, heat bonds, pressure bonds, heat and pressure bonds, or any other attachment mechanism known to those skilled in the art. The attachments 74 and 76 can also include a mechanical fastener, such as by sewing with thread, using buttons and button holes, using snaps, by employing hook and loop fasteners, etc. A hook and loop fastener is generally considered a releasable attachment. One type of hook and loop fastener is VELCRO® wherein a hook material is releasably engaged into a loop material. VELCRO® is a registered trademark of Velcro USA, Inc. having an office at 406 Brown Avenue, Manchester, N.H. 03103.

The attachments 74 and 76 can be formed along a continuous line or over a surface area having a predetermined length and width. Alternatively, the attachments 74 and 76 can consist of intermittent point bonds that are spaced apart from one another. For example, the intermittent point bonds can be formed by using a hot or cold melt adhesive or by forming ultrasonic bonds. Various bond formations can be used which are known to those skilled in the art. Desirably, the attachments 74 and 76 are formed using intermittent bonds because it allows the elastic material forming the front and back panels,. 12 and 24 respectively, to gather the absorbent assembly 56 as the elastic contracts. This gathering feature causes the absorbent assembly 56 to remain in direct contact with the user's body prior to and during the time period that the absorbent assembly 56 is being insulted with body fluid.

The front and back panels, 12 and 24 respectively, can be stretched in a direction approximately parallel to the transverse axis Y-Y, or in any other direction or directions, before the absorbent assembly 56 is secured to it. The amount of stretch can vary. No stretch is required if one does not wish to do so. Desirably, the front and back panels, 12 and 24 respectively, are stretched at least about 5% from a relaxed state before the absorbent assembly 56 is secured thereto. Desirably, the front and back panels, 12 and 24 respectively, are stretched at least about 10% from a relaxed state before the absorbent assembly 56 is secured thereto. More desirably, the front and back panels, 12 and 24 respectively, are stretched at least about 25% from a relaxed state before the absorbent assembly 56 is secured thereto. Most desirably, the front and back panels, 12 and 24 respectively, are stretched from between about 25% to about 1,000% from a relaxed state before the absorbent assembly 56 is secured thereto. The front and back panels, 12 and 24 respectively, extend laterally beyond the first and second side edges, 70 and 72 respectively, of the absorbent assembly 56. The front panel 12 also extends longitudinally beyond the first end 66 of the absorbent assembly 56 and the back panel 24 extends longitudinally beyond the second end 68 of the absorbent assembly 56. This size configuration of the front and back panels, 12 and 24 respectively, allow them to elastically conform to the torso of the wearer.

Still referring to FIG. 2, when the absorbent assembly 56 is secured to the front and back panels, 12 and 24 respectively, a crotch region 78 is formed. The crotch region 78 separates the front panel 12 from the back panel 24 and is designed to cover the perineum area of the wearer. The crotch region 78 can cover a distance of a few inches in an infant diaper to several inches in an adult incontinence garment. For example, a crotch region 78 in an infant diaper may range from about 2 inches (about 5 centimeters (cm)) to about 10 inches (about 25 cm); while in an adult incontinence garment, the crotch region 78 may range from about 6 inches (about 15 cm) to about 20 inches (about 51 cm).

The absorbent assembly 56 can be stretchable or non-stretchable in relation to the front and back panels, 12 and 24 respectively. Desirably, the absorbent assembly 56 is non-stretchable in relation to the front and back panels, 12 and 24 respectively. By having the absorbent assembly 56 be non-stretchable in relation to the front and back panels, 12 and 24 respectively, it is meant that the absorbent assembly 56 will not stretch appreciably in the longitudinal or transverse directions. The reason for this is that the front and back panels, 12 and 24 respectively, are elastically stretchable and can extend and retract to snugly conform to the user's anatomy, especially to his or her torso. Alternatively, the absorbent assembly 56 could be constructed with a pleated or folded construction, so as to be capable of being expanded in the longitudinal or transverse directions, if expansion of the absorbent assembly 56 is needed. The pleating or folding should occur before the absorbent assembly 56 is secured to the front and back panels, 12 and 24 respectively.

Normally, there is no need to have the absorbent assembly 56 gather as the front and back panels, 12 and 24 respectively, retract. However, the absorbent assembly 56 can be constructed and attached to the front and back panels, 12 and 24 respectively, in a way that will allow the absorbent assembly 56 to be gathered as the front and back panels, 12 and 24 respectively, elastically retract in the transverse direction. In either circumstance, the absorbent assembly 56 should remain over the perineum. As the absorbent assembly 56 receives body fluid and/or excrement discharged by the wearer, it will be displaced outward, away from the user's torso. The attachments 74 and 76 assure that the absorbent assembly 56 covers the perineum but is capable of moving outward away from the torso as additional body fluid is received and retained.

Still referring to FIGS. 2 and 3, the disposable pant-like undergarment 10 also has at least one elastic member 80 positioned adjacent to and aligned approximately parallel to each of the first and second side edges 70 and 72 of the absorbent assembly 56. Each of the elastic members 80 is situated between the bodyside liner 58 and the outer cover 60. Each of the elastic members 80 provides a gasket to hold the side edges 70 and 72 of the absorbent assembly 56 against the user's body. Each of the elastic members 80 can be in the form of an elastic strand, ribbon or strip. Desirably, there are from about 2 to 6 elastic members 80 positioned adjacent to each of the side edges 70 and 72. In FIGS. 2 and 3, two elastic members 80 are shown positioned adjacent to each of the side edges 70 and 72. The elastic members 80 can have a cross-sectional configuration that is round, square, rectangular or any other desired geometrical configuration. The elastic members 80 can be aligned parallel to the longitudinal axis X-X and should extend completely through the crotch region 78. Desirably, the ends of the elastic members 80 will be located within the front and back panels, 12 and 24 respectively.

Referring again to FIGS. 1 and 2, the absorbent assembly 56 is capable of being folded transversely, approximate the transverse axis Y-Y. The folding enables the front panel 12 to overlap the back panel 24 and the elastic band 42. When the absorbent assembly 56 is folded, the first and second side edges 20 and 22 of the front panel 12 will align with the first and second side edges 32 and 34 of the back panel 24 and the first and second side edges 48 and 50 of the elastic band 42. After being folded, a pair of seams 82 and 84 is formed to join the front panel 12 to both the back panel 24 and the elastic band 42. The seam 82 secures the first side edge 20 of the front panel 12 to both the first side edge 32 of the back panel 24 and the first side edge 48 of the elastic band 42. The other seam 84 secures the second side edge 22 of the front panel 12 to both the second side edge 34 of the back panel 24 and the second side edge 50 of the elastic band 42. After the pair of seams 82 and 84 is formed, the pant-like undergarment 10 has a waist opening 86 and a pair of leg openings 88 and 90. Since the front and back panels, 12 and 24 respectively, are formed from a stretchable elastic material, the pair of leg openings 88 and 90 can expand or retract in size to accommodate the anatomy of the user.

Referring to FIGS. 1–3, the disposable pant-like absorbent undergarment 10 can also include one or more leg elastics 92 and 94 positioned in the front and back panels, 12 and 24 respectively, approximate the leg openings 88 and 90. Each of the leg elastics 92 and 94 is shown consisting of three elastic strands, see FIG. 2, although it should be understood that from 1 to about 10 elastic strands 92 and 94 could be used, if desired. The leg elastics 92 and 94 can be positioned between the first and second layers, 36 and 38 respectively, as shown. Alternatively, the leg elastics 92 and 94 can be positioned between the second and third layers, 38 and 40 respectively, if desired. Normally, the leg elastics 92 and 94 are aligned approximately parallel to the edges of the front and back panels, 12 and 24 respectively. Such edges are located adjacent to the crotch region 78 of the absorbent assembly 56. The leg elastics 92 and 94 can be uniformly or randomly spaced apart from one another and are normally located within about 0.3 inches (about 0.76 cm) of the leg openings 88 and 90.

Figure 5:
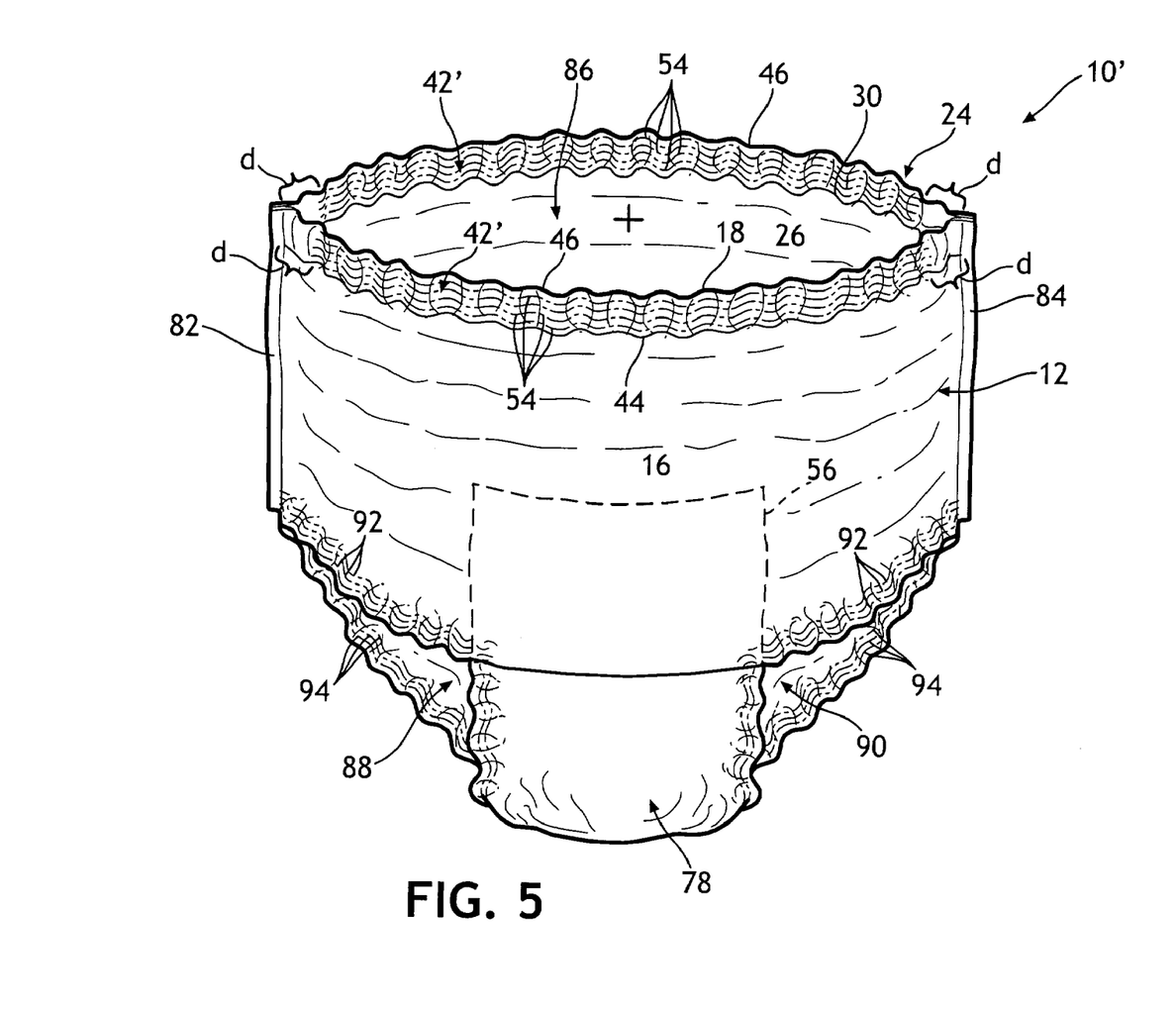
FIG. 5 is a perspective view of an alternative embodiment of a disposable pant-like undergarment having an elastic band secured to the front and back panels and extending substantially around the entire waist opening.
Figure 6:
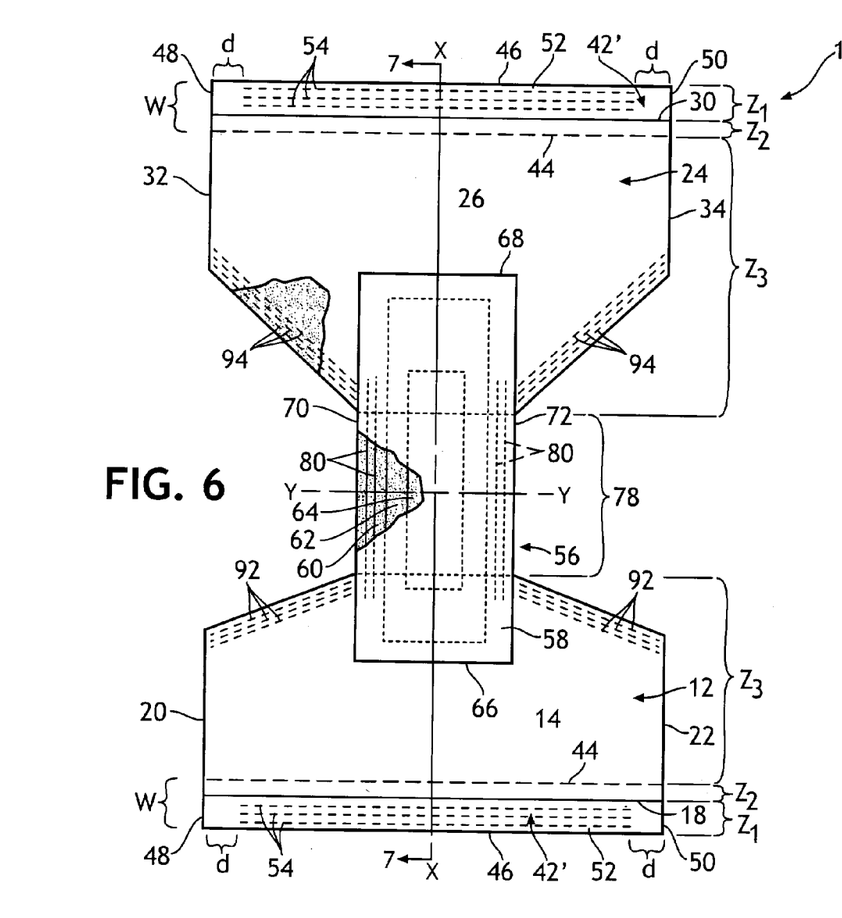
FIG. 6 is a plane view of the disposable pant-like undergarment shown in FIG. 5. depicting an absorbent assembly secured to the inner surface of the stretchable front and back panels and showing two partial cut away views of the construction of the absorbent assembly and the leg elastics.
Figure 7:
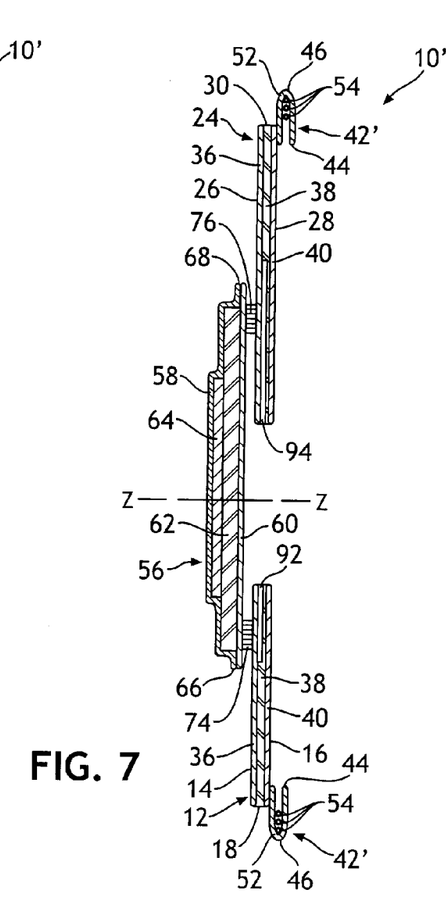
FIG. 7 is a side view of the disposable pant-like undergarment shown in FIG. 6 and taken along line 7—7.

Referring now to FIGS. 5–7, an alternative embodiment is shown for a disposable pant-like undergarment 10'. For ease of understanding, like numerals will be used in FIGS. 5–7 for the pant-like undergarment 10'. The disposable undergarment 10' is similar to that shown in FIGS. 1–3 except for three major differences. The first difference is that a pair of elastic bands 42' is present. One of the elastic bands 42' is secured to the front panel 12 and the other elastic band 42' is secured to the back panel 24. The pair of elastic bands 42' will cooperate and form a single waist band extending around the circumference of the disposable pant-like undergarment 10' when the seams 82 and 84 are formed. Each elastic band 42' has first and second side edges, 48 and 50 respectively, and each is cantilevered outward from the distal ends 18 and 30 of the front and back panels, 12 and 24 respectively. As described with reference to FIGS. 1–3, each of the pair of elastic bands 42' has a retracted length that is less than the retracted length of the panel to which it is secured. The retracted length is measured as was described above with reference to FIGS. 1–3. Furthermore, each of the pair of elastic bands 42' has a width (w) that ranges from between about 3 mm to about 150 mm.

A second difference in the embodiment shown in FIGS. 5–7 is that each of the pair of elastic bands 42' contains only three elastic strands 54 instead of the four elastic strands 54 that were used in the elastic band 42. All three of the elastic strands 54 are situated between the distal edges 18 and 30 of the front and back panels, 12 and 24 respectively, and the second end 46 of the elastic bands 42'. This means that no elastic strand 54 is present in the second zone ($z_2$). By constructing the second zone ($z_2$) to be devoid of any elastic strands 54, the force needed to expand the second zone ($z_2$) will change. The amount of change can vary. However, the force required to stretch the second zone ($z_2$) from its retracted length will be greater than the force required to stretch the first zone ($z_1$) from its retracted length. Likewise, the force required to stretch said first zone ($z_1$) from its retracted length will be greater than the force required to stretch said third zone ($z_3$) from its retracted length.

A third difference in the embodiment shown in FIGS. 5–7 is that the elastic strands 54 in the pair of elastic bands 42' do not extend from the first side edge 48 to the second side edge 50. Instead, the elastic strands 54 stop short of the first and second side edges, 48 and 50 respectively, by a distance (d). The distance (d) can vary in dimension. Desirably, the distance (d) ranges from between about 1 mm to about 100 mm. More desirably, the distance (d) ranges from between about 2 mm to about 50 mm. Even more desirably, the distance (d) ranges from between about 3 mm to about 25 mm. Most desirably, the distance (d) ranges from between about 5 mm to about 12 mm. By not running the elastic strands 54 to the first and second side edges, 48 and 50 respectively, one can be assured that the elastic strands 54 will not interfere in forming the seams 82 and 84. In some cases, it is easier to ultrasonically, thermally or adhesively bond two materials together when the elastic strands 54 or an elastic layer is not present. Usually a stronger and more uniform bond or attachment can be obtained.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A disposable pant-like undergarment comprising:
    a) a stretchable front panel having a distal end, first and second side edges, and a retracted length measured between said first and second side edges;
    b) a stretchable back panel having a distal end, first and second side edges, and a retracted length measured between said first and second side edges;
    c) an elastic band secured to only one of said front and back panels and having a first end and first and second side edges, said elastic band being cantilevered outward from said distal end such that said first end overlaps a portion of said respective front or back panel, and said elastic band having a retracted length less than said retracted length of said panel to which it is secured;
    d) an absorbent assembly including a liquid pervious bodyside liner, a liquid-impervious outer cover, and an absorbent positioned therebetween, said absorbent assembly being secured to said front and back panels, and said absorbent assembly capable of being folded to enable said front panel to overlap said back panel; and
    e) a pair of seams joining said front panel, back panel and elastic band together at said first and second side edges to form a pant-like undergarment having a waist opening and a pair of leg openings, said elastic band creating a snug fit at said waist opening.

2. The disposable pant-like undergarment of claim 1 wherein said elastic band cooperates with said panel to which it is secured to form a three-zone stretchable structure.

3. The disposable pant-like undergarment of claim 2 wherein said three-zone stretchable structure includes a first zone, a second zone and a third zone, and force required to stretch said second zone is greater than the force required to stretch said first zone, and the force required to stretch said first zone is greater than the force required to stretch said third zone.

4. The disposable pant-like undergarment of claim 1 wherein said elastic band has a retracted length that is at least 2% less than said retracted length of said panel to which it is secured.

5. The disposable pant-like undergarment of claim 1 wherein said elastic band has a retracted length that is at least 50% less than said retracted length of said panel to which it is secured.

6. The disposable pant-like undergarment of claim 1 wherein said elastic band is a folded non-elastic member enclosing at least one elastic strand.

7. The disposable pant-like undergarment of claim 1 wherein said elastic band has a retracted length that is at least 0.25 inches shorter than said retracted length of said panel to which it is secured.

8. The disposable pant-like undergarment of claim 1 wherein said elastic band contains at least one elastic strand that extends from said first side edge to said second side edge.

9. The disposable pant-like undergarment of claim 8 wherein said elastic band contains at least one elastic strand that does not extend from said first side edge to said second side edge.

10. The disposable pant-like undergarment of claim 1 wherein said elastic band is folded over upon itself.

11. The disposable pant-like undergarment of claim 10 wherein said elastic band has a second end and said fold is aligned adjacent to said second end.

12. A disposable pant-like undergarment comprising:
a) a stretchable front panel having an inner surface, an outer surface, a distal end, first and second side edges, and a retracted length measured between said first and second side edges;
b) a stretchable back panel having an inner surface, an outer surface, a distal end, first and second side edges, and a retracted length measured between said first and second side edges;
c) an elastic band secured to said outer surfaces of at least one of said front and back panels and having a first end and first and second side edges, said elastic band being cantilevered outward from at least one of said distal ends such that said first end overlaps a portion of at least one of said front and back panels, and said elastic band having a retracted length less than said retracted length of said panel to which it is secured;
d) an absorbent assembly including a liquid perilous bodyside liner, a liquid-impervious outer cover, and en absorbent positioned therebetween, said absorbent assembly being secured to said inner surfaces of said front and back panels, and said absorbent assembly capable of being folded to enable said front panel to overlap said back panel; and
e) a pair of seams joining said front panel, back panel and elastic band together at said first and second side edges to form a pant-like undergarment having a waist opening and a pair of leg openings, said elastic band creating a snug fit at said waist opening.

13. The disposable pant-like undergarment of claim 12 wherein said elastic band contains at least one elastic strand that extends from said first side edge to said second side edge.

14. The disposable pant-like undergarment of claim 12 wherein said elastic band contains at least one elastic strand that does not extend from said first side edge to said second side edge.

15. The disposable pant-like undergarment of claim 12 wherein said elastic band has a retracted length that is at least 10% less than said retracted length of said panel to which it is secured.

16. The disposable pant-like undergarment of claim 12 wherein said elastic band has a retracted length that is at least 15% less than said retracted length of said panel to which it is secured.

17. The disposable pant-like undergarment of claim 12 wherein said elastic band has a width ranging from between about 3 millimeters to about 150 millimeters.

18. The disposable pant-like undergarment of claim 12 wherein said elastic band is folded over upon itself.

19. The disposable pant-like undergarment of claim 18 wherein said elastic band has a second end and said fold is aligned adjacent to said second end.

20. A disposable pant-like undergarment comprising:
a) a stretchable front panel having an inner surface, an outer surface, a distal end, first and second side edges, and a retracted length measured between said first and second side edges;
b) a stretchable bad panel having an inner surface, an outer surface, a distal end, first and second side edges, and a retracted length measured between said first and second side edges;
c) a pair of elastic bands secured to said outer surfaces of both said front and back panels, each elastic band having a first end and first and second side edges, each of said pair of elastic bands being cantilevered outward from said distal end of one of said front and back panels such that said first end overlaps a portion of said respective front and back panels, and each of said pair of elastic bands having a retracted length less than said retracted length of said panel to which it is secured;
d) an absorbent assembly including a liquid pervious bodyside liner, a liquid-impervious outer cover, and an absorbent positioned therebetween, said absorbent assembly being secured to said inner surfaces of said front and back panels, and said absorbent assembly capable of being folded to enable said front panel to overlap said back panel; and
e) a pair of seams joining said front panel, back panel and elastic band together at said first and second side edges to form a pant-like undergarment having a waist opening and a pair of leg openings, said pair of elastic bands creating a snug fit at said waist opening.

21. The disposable pant-like undergarment of claim 20 wherein each of said pair of elastic bands has a width ranging from between about 3 millimeters to about 150 millimeters.

22. The disposable pant-like undergarment of claim 20 wherein each of said pair of elastic bands contains at least one elastic strand that does not extend from said first side edge to said second side edge.

23. The disposable pant-like undergarment of claim 20 wherein said elastic band has a retracted length that is at least 10% less than said retracted length of said panel to which it is secured.

24. The disposable pant-like undergarment of claim 20 wherein said elastic band has a retracted length that is at least 15% less than said retracted length of said panel to which it is secured.

25. The disposable pant-like undergarment of claim 20 wherein said elastic band is folded over upon itself.

26. The disposable pant-like undergarment of claim 25 wherein said elastic band has a second end and said fold is aligned adjacent to said second end.

* * * * *